United States Patent [19]
Cochrum

[11] Patent Number: 5,510,102
[45] Date of Patent: Apr. 23, 1996

[54] PLASMA AND POLYMER CONTAINING SURGICAL HEMOSTATIC ADHESIVES

[75] Inventor: Kent C. Cochrum, Davis, Calif.

[73] Assignee: The Regents of the University of California, Oakland, Calif.

[21] Appl. No.: 377,775

[22] Filed: Jan. 23, 1995

[51] Int. Cl.$^6$ .......................... A61K 38/36; A61L 25/00
[52] U.S. Cl. .................. 424/78.08; 424/530; 602/52; 128/DIG. 22
[58] Field of Search ...................... 514/772.2; 424/78.08, 424/530

[56] References Cited

U.S. PATENT DOCUMENTS

| | | | |
|---|---|---|---|
| 4,373,519 | 2/1983 | Errede et al. | 128/156 |
| 4,599,209 | 7/1986 | Dautzenberg et al. | 264/7 |
| 4,664,105 | 5/1987 | Dautzenberg et al. | 128/156 |
| 5,226,877 | 7/1993 | Epstein | 604/35 |
| 5,292,362 | 3/1994 | Bass et al. | 106/124 |

*Primary Examiner*—Peter F. Kulkosky
*Attorney, Agent, or Firm*—Hana Verny

[57] ABSTRACT

Autologous platelet-rich plasma and a biocompatible polymer containing hemostatic adhesive agents. The agents have strong hemostatic properties when applied to a bleeding wound or vessel.

17 Claims, 2 Drawing Sheets

FIGURE 2

HEMOSTASIS USING A HEMOSTATIC ADHESIVE PLASMA/POLYMER AGENT

PLASMA AND POLYMER CONTAINING SURGICAL HEMOSTATIC ADHESIVES

BACKGROUND OF THE INVENTION

FIELD OF INVENTION

This invention concerns novel type of hemostatic adhesives. In particular, this invention concerns the hemostatic and adhesive plasma and polymer containing adhesives prepared from the platelet-rich plasma concentrate and from a biocompatible polymer. In the preferred form, the plasma is obtained from the patient's own blood to avoid undesirable immunogenic reactions. The adhesive has strong hemostatic properties when applied to a bleeding wound or vessel where it facilitates a rapid formation of a polymer clot and where the plasma proteins and platelet quickly trigger the normal clotting mechanism.

BACKGROUND ART AND RELATED ART DISCLOSURES

Surgical biological glues have recently been used in a variety of surgical procedures. Among those most known and used are a fibrin glue or a gelatin-resorcin-formalin glue.

Fibrin glue is based on the basic physiological fibrinogen function. In the presence of calcium ions, activation of fibrinogen and fibrin-stabilizing factor XIII with thrombin produces a stable fibrin clot. Fibrin itself adheres to collagen, and factor XIII stimulates increased collagen biosynthesis by activating fibroblasts. The application of fibrin glue in wound healing allows restoration of the structural properties of the wound by the glue and stimulation of repair by the components that comprise the glue. Fibronectin and cold insoluble globulin also enhance fibroblast proliferation.

Current methods of preparing fibrin glue have improved recovery of a variety of coagulation proteins including clotting factors and thrombin.

While hemostatic action of fibrin glue have been described and shown to act as a hemostatic agent in hepatic and splenic trauma *J. Ped. Surg.*, 24:867 (1989), as a sealant of the common bile duct *Surgery*, 101:357 (1987), as a glue sealing pancreatic injuries *Am. J. Surg.*, 161:479 (1991), resections and anastomosis *Brit. J. Plast. Surg.*, 42:54 (1989), as a glue for microvascular anastomosis, as a glue for treating aortic dissections *Ann. Thorac. Surg.*, 50:143 (1990), its toxicity and possible anaphylactic reactions are of great concern. Fatal reaction to the use of fibrin glue in deep hepatic wounds is described in *J. Trauma*, 31:408 (1991). This fatal reaction is believed to have been caused by activation and conversion of fibrinogen into a fibrin with a bovine thrombin resulting in anaphylactic shock leading to death.

The most common method of preparation of fibrin glue is by the simultaneous mixing of concentrated fibrinogen complex obtained from pooled human blood, the bovine thrombin and ionic calcium immediately before use. The addition of the nonhuman, typically bovine thrombin in the fibrin glue preparations used for treatments in humans has resulted in severe and even fatal anaphylactic reactions, such as described above. Hemostasis abnormalities caused by antibodies to bovine proteins, such as bovine thrombin, which cross-react with human proteins, including thrombin and factor V have been reported in *J. Thorac. Cardiovac. Surg.*, 105:892 (1993). Similarly, foreign body reactions following the use of these fibrin bovine thrombin containing glues have been detected and described in *Eur. J. Pediatr. Surg.*, 2:285 (1992).

Another major problem connected with currently used fibrin glues is due to the use of pooled human blood which may result in transmission of infectious diseases to a patient treated with the fibrin glue obtained from the human donors, as described in *Opth. Surg.*, 23:640 (1992).

Additionally, while fibrin glues set very rapidly, from three to five seconds, there is no increase in their adhesive strength after five minutes (*J. Biomed. Mater. Res.*, 26:481 (1992)).

It would be, therefore, advantageous to provide a new type of a biological hemostatic adhesive which would eliminate or reduce the use of bovine thrombin, or thrombin obtained from human donors, which can lead to a formation of antibodies to such bovine or human proteins, or which adhesive would avoid pooling of human blood which may result in transmission of infectious diseases. The new type of the hemostatic adhesive would avoid problems associated with the currently available fibrin glues. It would also be advantageous to provide a hemostatic adhesive agent acting rapidly and possessing an ability to increase its adhesivity in a cascade-like fashion.

It is, therefore, a primary object of this invention to provide a novel type of hemostatic adhesive agents for surgical and other medical purposes. In the most preferred form, these agents are prepared from autologous blood. The new agents provide rapid hemostasis by cascade-like effect and have a considerable adhesive strength. The new agents eliminate or strongly reduce the risk of disease transmission. The new agents eliminate or strongly reduce the risk of immunogenic reactions. The new agents significantly promote healing of tissues and are additionally less expensive than currently available glues. The novel type of such hemostatic adhesive agents is prepared from the platelet-rich plasma, preferably from the patient's own blood, combined with various biocompatible polymers.

The autologous platelet-rich plasma and biocompatible polymer containing agents useful as an hemostatic surgical adhesives have not been previously reported or disclosed.

All patents, patent applications and references cited herewithin are hereby incorporated by reference.

SUMMARY

One aspect of the invention is a hemostatic adhesive agent comprising a platelet-rich plasma concentrate and a biocompatible polymer.

Another aspect of the invention is a hemostatic adhesive agent comprising an autologous platelet-rich plasma concentrate and a biocompatible polymer.

Still another aspect of the invention is a hemostatic adhesive agent comprising a platelet-rich plasma concentrate and an alginate.

Still yet another aspect of the invention is a hemostatic adhesive agent comprising a platelet-rich plasma concentrate and a chitosan.

Still yet another aspect of the invention is a hemostatic adhesive agent comprising a platelet-rich plasma concentrate and poly-L-lysine.

Still yet another aspect of the invention is a hemostatic adhesive agent formed in situ at a place of injury or bleeding.

Still another aspect of the invention is a method of use of a hemostatic adhesive agent for rapid clotting to provide rapid hemostasis in a cascade-like fashion.

DEFINITIONS

As used herein:

"Hemostatic adhesive agent" also called "plasma/polymer" means a solution or other preparation which contains essentially two components: a platelet-rich plasma concentrate and a physiologically acceptable biocompatible and FDA approved polymer.

"Platelet-rich plasma" means "concentrated plasma" containing the same volume of platelets which would be present in the normal volume of plasma before its concentration.

"Concentrated plasma" means normal plasma obtained by any means typically used for separating plasma from other blood components, concentrated 5 to 10 times of its original volume. The concentrated plasma thus contains in 5–10 times smaller volume, the same amount of plasma proteins which are present in the normal nonconcentrated volume.

"Cascade-like effect" means a sequence of reactions beginning with applying the hemostatic agent of the invention to the wound or incision, where the polymer contained in the hemostatic agent quickly gels into a polymer clot. This clot rapidly triggers release of factors Va, Xa and thromboplastins from the exogenous platelets present in the platelet-rich plasma component of the hemostatic agent. The release of thromboplastins from these exogenous platelets initiate the physiological clotting process. Since the polymer is not a natural substrate for plasmin/plasminogen lytic reactions, the hemostatic reaction continues unabated until the hemostasis is achieved.

"Exogenous platelets" are platelets present in the platelet-rich plasma concentrate.

"Endogenous platelets" are platelets present in the circulating blood of the patient.

DETAILED DESCRIPTION OF THE INVENTION

The current invention concerns a novel type of hemostatic adhesive agents. These agents are prepared from and contain the platelet-rich plasma concentrate in combination with physiologically acceptable biocompatible polymers. The combination of the plasma concentrate with the polymers forms, in the presence of calcium ions, an adhesive which has very strong adhesive properties, and very rapid onset of these adhesive properties. The length of action of these adhesives is controlled by the polymer gelling. Adhesivity strength and the length of the hemostatic action depend on the type and on the amount of the polymer. Hemostasis is achieved in cascade-like fashion caused by rapid and continuous activation and aggregation of the exogenous platelets present in the platelet-rich plasma. Due to this cascade-like effect, the adhesing strength of the hemostatic agent increases well beyond the time (3–5 minutes) during which the maximal adhesive strength is obtained physiologically or with fibrin glues, and continues until the complete hemostasis occurs.

One aspect and one of the advantages of the invention is that the platelet-rich plasma is prepared from the patient's own blood, thereby eliminating possible immunogenic reactions as well as transmission of infectious diseases, toxins or parasites. The hemostatic adhesive agents of the invention promote and accelerate wound healing because they are made of the patient's own blood components. In alternative, the biocompatible polymer alone is useful as a hemostatic agent when applied in a concentration sufficient to accomplish hemostasis.

I. Normal Physiological Mechanism of Blood Coagulation

Physiological mechanism of blood coagulation and clotting is based on properties of plasma and platelets. These two blood components contain all the factors required for clotting.

Figure 1:
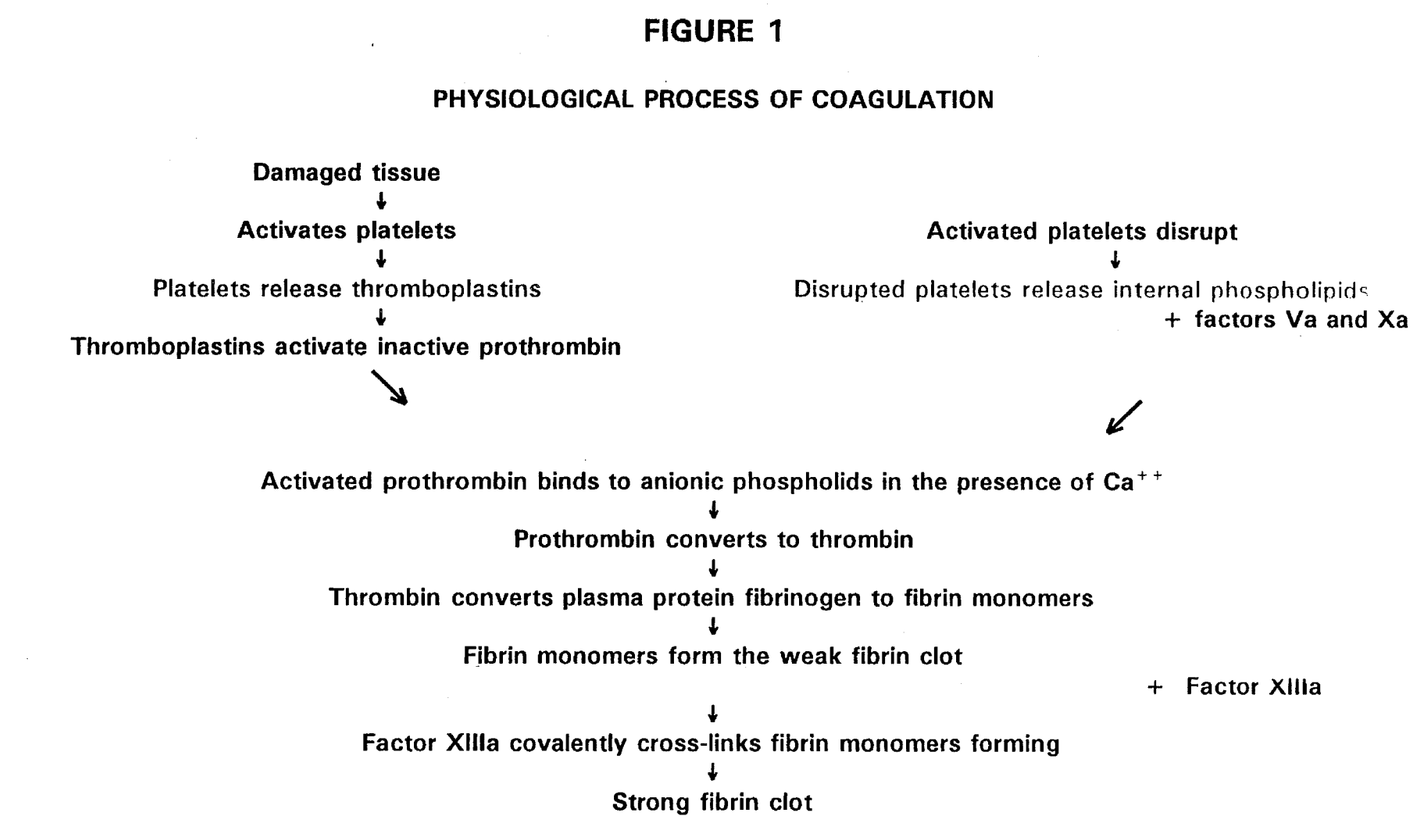
FIG. 1 is a scheme illustrating a physiological process of coagulation.

Processes involved in blood clotting are seen in FIG. 1.

Two major plasma proteins involved in blood clotting are fibrinogen and prothrombin. The essential reaction in coagulation of the blood is the enzymatic conversion of the soluble protein fibrinogen into the insoluble protein fibrin by thrombin. Fibrinogen exists in the circulating blood as such. Thrombin is formed from an inactive circulating precursor, prothrombin, during the tissue injury, bleeding or blood loss. The activation of prothrombin depends on the presence of calcium ions ($Ca^{++}$) and on the presence of thromboplastins which are released or derived from the damaged tissues, from the disintegrating platelets or from the plasma itself.

Normally, when the tissue is injured, it responds physiologically by activation of platelets followed by a release of thromboplastins. Thromboplastin (plasma factor III) is a substance that assists in the clotting of the blood by initiating the conversion of the inactive prothrombin (plasma factor II) to the active thrombin. Such conversion occurs in the presence of calcium ions (plasma factor IV). Thrombin is the blood enzyme that causes clotting by converting fibrinogen (plasma factor I) to fibrin.

Thrombin is a very potent serine protease which can coagulate at least 600 times their weight of fibrinogen. Thrombin is a protein with a molecular weight of about 34,000. The velocity of the thrombin-fibrinogen reaction is accelerated by increasing the concentration of thrombin.

Thrombin acts enzymatically to split off a highly acidic fibrinopeptide from the fibrinogen. The remainder of the fibrinogen then polymerizes to form fibrin. Thrombin can act in the absence of $Ca^{++}$. Fibrin is an elastic, thread-like insoluble protein forming the network of the clot.

Thrombin enzymatically hydrolyses arginine-glycin peptide bonds in fibrinogen thereby generating fibrin monomers. These insoluble fibrin monomers spontaneously associate in a regularly staggered array to form the insoluble fibrin polymer clot. The initial fibrin clot formed within first 3–5 seconds is rather weak one, held together only by the noncovalent array of these fibrin monomers.

Additionally, thrombin converts fibrin stabilizing factor XIII, to active factor XIIIa. Factor XIIIa is an enzyme transglutaminase which covalently cross-links a fibrin monomers by forming specific isopeptide bonds thereby strengthening the fibrin clot. The freshly formed threads are extremely adhesive, sticking to each other, to the blood cells, to the tissues, and to certain foreign surfaces. This adhesiveness makes the clot an effective haemostatic agent. All these enzymatic reactions, of course, take certain time, typically between 3–5 minutes, within which the final hemostatic clot forms.

Aside of fibrinogen, prothrombin, thromboplastin, and calcium (plasma factors I and IV), there are other plasma factors involved in the normal physiological coagulation reactions. These factors are plasma factors proaccelerin (V), proconvertin (VII), antihemophilic globulin (VIII), Christmas factor (IX), Stuart-Prower factor (X), plasma thromboplastin antecedent (XI), Hageman factor (XII) and fibrin stabilizing factor (XIII). Plasma factor V (proaccelerin) acts, when activated to factor Va, as a cofactor for the activated enzyme factor Xa that activates prothrombin. These and all other above named factors are involved in the normal blood coagulation processes.

Calcium ions are essential for clotting. They are necessary for the formation of active thromboplastin and for the conversion of prothrombin to thrombin in the first phase of the coagulation process. They are not necessary and do not influence the action of thrombin on fibrinogen in the second phase of the coagulation.

The activation of prothrombin occurs on the platelets and requires platelet anionic phospholipid, activated factor Va, activated factor Xa and calcium ions. The platelet anionic phospholipids, which are normally situated on the internal side of the platelet plasma membrane, are exposed as a result of the platelet disruption. These phospholipids bind $Ca^{++}$ and prothrombin. Prothrombin activates factor V, normally present in platelets to which is activated by Va factor. Activated Va factor binds to specific receptor on the platelet membrane and by itself Va factor acts as a receptor for factor Xa. Factor Xa binds prothrombin and, itself being a serine protease, cleaves the inactive amino portion of prothrombin, thereby activating prothrombin to thrombin.

Under normal physiological circumstances, regulatory mechanisms are present that prevent activated coagulation reactions from proceeding unchecked after hemostasis is achieved. If not controlled, such activated coagulation (hemostasis) could cause either local thrombosis or disseminated intravascular coagulation. These regulatory mechanisms include fibrinolytic system, cellular clearance of activated clotting factors, and neutralization within the blood of the enzymes and activated cofactors of coagulation.

The fibrinolytic system activates fibrin deposition. By dissolving fibrin, this system helps keep open the lumen of an injured blood vessel and presents formation of thrombin. A balance between fibrin deposition and lysis maintains and remolds the hemostatic seal during the days required to repair the injured vessel wall.

The enzyme plasmin catalyzes the lysis of fibrin. Plasmin arises from an inert plasma precursor, plasminogen, through cleavage of a single Arg-Val peptide bond in plasminogen. Materials that can catalyze this cleavage are plasminogen activators. Plasmin is a powerful proteolytic enzyme that degrades fibrin, first into large fragments, and then into smaller soluble fragments. These soluble fragments, referred to collectively as fibrin degradation products, are swept into the circulation.

When fibrinogen is converted to fibrin, lysine residues become available on the molecule to which plasminogen can bind tightly by way of special sites on plasminogen called lysine binding sites. Plasminogen activators triggering lysis of intravascularly deposited fibrin are released from vascular endothelial cells.

The above-discussed coagulation properties of fibrinogen are widely utilized for fibrin glues. These glues are typically prepared from fibrinogen obtained from bovine or pooled human blood and from bovine or human thrombin. These foreign proteins may lead to a development of recipients' immunoreactions in case of use of different species fibrinogen or thrombin, or in transfer of infections between individuals from the use of fibrinogen and/or thrombin of the same species.

II. Hemostatic Adhesive Agent of the Invention

Hemostatic adhesive agents of the invention and their hemostatic action differ from the prior fibrin glues. The hemostatic agent according to the invention is typically prepared from platelet-rich plasma, in a combination with a physiologically acceptable polymer. The hemostatic adhesive agent consists of isolated platelets and plasma concentrate containing a 5–10 times higher concentration of fibrinogen, and other plasma proteins than is the normal concentration of these components in regular plasma. The combination of plasma concentrate and platelets promote clotting, adhesion and healing.

The hemostatic agent additionally contains the physiologically acceptable biocompatible polymer which gels upon contact with calcium or other divalent cations forming a polymer gel clot. This polymer causes rapid activation and aggregation of both exogenous and endogenous platelets and red cells and thereby induces and increases hemostatic adhesion in a cascade-like manner. In alternative, the biocompatible polymer can be used alone as the hemostatic adhesive agent.

In its most preferred form, the hemostatic adhesive agent is autologous, that is, it is prepared from the patient's own blood combined with the physiologically acceptable biocompatible polymers approved by the Food and Drug Administration for use in humans. The hemostatic agent of the invention is preferably prepared in the operating room at the time of surgery.

Figure 2:
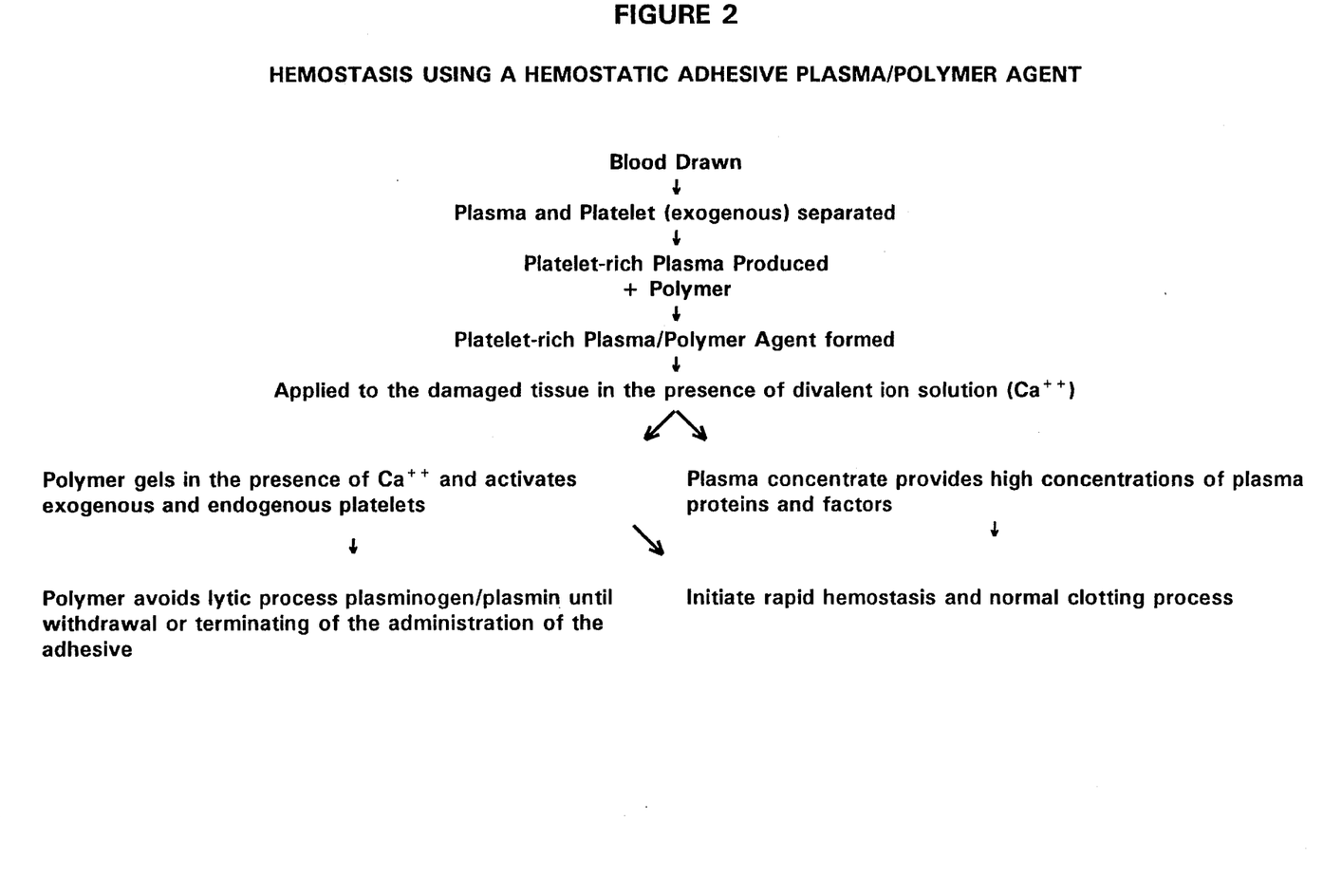
FIG. 2 is a scheme illustrating a hemostatic process using the current invention.

Process for hemostasis according to the invention using hemostatic adhesive agents of the invention, is illustrated in FIG. 2.

The hemostatic plasma/polymer agent has a high ratio of the platelet-rich plasma concentrate to the polymer. Generally, the agent is composed of about 80%–98% concentrated, preferably autologous platelet-rich plasma and from about 2% to about 20% of the polymer. When mixed and applied to a wound surface or bleeding vessel, the polymer component gels in the presence of divalent cations such as calcium and on contact with the bleeding wound aggregates and activates the exogenous and endogenous platelets. Activated platelets release thromboplastin. The gelled polymer forms the initial hemostatic polymer clot within which the platelets or platelet debris is caught.

The exogenous platelet activation by the polymer initiates and enhances the normal physiological clotting system which reacts much faster than under the normal circumstances. The hemostatic polymer clot develops further in the presence of $Ca^{++}$ and plasma factors V and X, which are present in the concentrated plasma in a concentrated form, converting prothrombin to thrombin. Meanwhile, the gelled polymer activates more and more platelets in a cascade-like fashion, enlarges the original polymer clot and also forms a clot matrix.

Such clot matrix is, under normal physiological conditions formed only after the chain of reactions happens including the activation of platelets leading to the activation of prothrombin to thrombin, the activation of fibrinogen by thrombin, the conversion of fibrinogen to initial fibrin monomers, the formation of the weak fibrin clot and strengthening of fibrin by cross-linking with factor XIIIa. The formed clot in response to the platelet activation then converts soluble fibrinogen to a stable fibrin clot. Such conversion occurs in the presence of factor XIIIa, a fibrin stabilizing factor, that catalyzes formation of peptide bonds between fibrin molecules and in this way stabilizes the clot.

To the contrary, in the current invention, the clot matrix is formed quickly following the application of the hemostatic adhesive of the invention to the site of injury or bleeding, as illustrated in FIG. 2.

As seen in FIG. 2, the hemostasis according to the invention, as compared to the normal physiological coagulation process shown in FIG. 1, is much faster, and it is initiated quickly. Strength of the hemostatic polymer clot can be increased for the entire time when the adhesive is applied. In the normal physiological coagulation process, after 3–5 minutes the strength of the normal clot does not increase. The new hemostatic process proceeds in controlled manner until complete hemostasis is achieved. Adhesivity of the agent is controlled by the higher or lower concentration of the added polymer and also by the concentration factor of the plasma proteins. When the concentration of polymer is from 2% to about 10%, then the tensil strength is lesser. When the polymer concentration is above 10% or if it is around 20% the tensil strength of the hemostatic clot is greater.

Using the current invention, the platelet-rich plasma is prepared as described below and in examples. A chosen polymer is then added to the concentrated platelet-rich plasma. Thus rapidly made adhesive is applied to the site of the injury, such as the wound, venous incision, cut or rupture or to the damaged tissue, which is first sprayed with a solution containing calcium or other divalent cations. Upon contact with the adhesive, such solution causes rapid gelling of the polymer. Gelling polymer acts as an extraneous impulse activating both a large volume of exogenously supplied and endogenously present platelets. Such large volume of exogenous platelets is provided by the platelet-rich plasma concentrate. Utilizing the highly concentrated plasma also provides for high concentrations of proteins, such as prothrombin, fibrinogen, and other clotting factors, present in the platelet-rich plasma concentrate. Upon applying the plasma concentrate-polymer to the site of injury, the physiological clotting begins rapidly and on the large scale, having already present and available all necessary clotting factors in high concentrations. Gelled polymer which forms the initial clot is becoming substantially strengthened by platelets and platelets debris and its adhesivity is additionally enhanced by the natural clotting processes.

Meanwhile, the polymer activates more and more platelets in cascade-like fashion so that the size and strength of the clot is much greater than that of the normal clot. Additionally, the polymer allows extension of time for the hemostatic polymer clot formation and for increase of the strength of the clot. Since the natural coagulation is endogenously regulated and controlled and is a subject to time related lysis, as described above, such regulation mechanisms limits strength of the adhesivity of normal clot to that formed within 3–5 minutes. After that time such strength of the normal clot cannot be increased. On the other hand, the polymer is not subject to lysis or to the other regulatory mechanisms and can therefore proceed unhindered for more than 30 minutes and up to several hours.

Hemostatic adhesive agents containing plasma/polymer have many advantages over other currently available fibrin glues. They provide rapid hemostasis and adhere the damaged tissues together with great strength. The presence of the polymer in the hemostatic agent allows sizable increase in the speed with which the clot is formed, increasing the clot size and strength in the cascade-like manner. The hemostatic adhesive also allows time control with respect to when to stop the clotting and clot formation. Since the autologous hemostatic plasma/polymer agents contain the patient's own viable platelets, they actually promote the healing process. Other advantages of plasma/polymer are the absence of foreign proteins, such as bovine and human fibrinogen or thrombin which foreign proteins may lead to immune reactions. Studies of the University of California, Davis have indicated that, for example, in trauma patients, excess autologous thrombin may also be detrimental. The reduced risk of the transmission of infectious and parasitic diseases, such as HIV and hepatitis, is also a major advantage because they may easily be transmitted, if the donor's blood is not properly tested for these diseases. The new hemostatic agents, prepared from the patient's own blood in the operating room just before use, eliminate such risk.

Previously known surgical fibrin glues made up of pooled human fibrinogen activated by bovine thrombin are used extensively in Europe and attempts have been made to introduced the glues in the United States. The FDA, however, has been reluctant to approve these fibrin glues because of the risk of animal and human viruses transmission and because of the immunological reactions caused by bovine thrombin. The current invention overcomes these problems and provides many additional advantages, as enumerated above.

1. Preparation of Platelet-rich Plasma

Platelet-rich plasma is prepared from the whole blood either of the patient to be treated (autologous plasma) or from the human plasma other than the patient (non-autologous plasma). In the latter case, care is taken to utilize only healthy and non-contaminated full blood. Additionally, in case of planned surgery, patient may provide his own blood before the operation so that the concentrated plasma is prepared in advance. In case of acute injuries or trauma, the hemostatic adhesive agent according to the invention is prepared at the time of operation or treatment. Thus, no blood bank, storage, prior collection of blood or isolation of platelets is necessary. However, the adhesive may be prepared from the blood available from the blood bank, if needs be. Under the most optimal conditions, the current adhesive can be prepared quickly without any risk that the patient may encounter immune reactions or become infected with the other individual blood.

The hemostatic adhesive agent is prepared from the whole blood by separating red blood cells from plasma and by isolating and separating isolated platelets. Typically, the whole blood is drawn into a buffered anticoagulant agent, such as sodium citrate, and centrifuged to separate the platelets and plasma from the red blood cells. Plasma is removed and centrifuged for the second time at high speed to separate the platelets and the plasma. Plasma is again removed and concentrated by factor 5–10, preferably by factor of about 7–8, by using any means suitable for concentration, preferably by filtration and/or under vacuum. Platelets precipitate is saved separately and ultimately added to the plasma concentrate.

2. Polymer Component of the Hemostatic Adhesive

A polymer added to the platelet-rich concentrated plasma is selected from the group containing alginates, poly-1-amino acids, chitosan or chitin. Polymer must gel upon contact with calcium ions or any other divalent cations.

The alginate polymer, such as sodium alginate, calcium alginate, strontium alginate, barium alginate, magnesium alginate or any other alginate or a mixture thereof, is added to the platelet-rich plasma concentrate in concentration from 0.001% to about 20%, preferably from about 0.1% about 10%.

In alternative, the polymer is selected from the group consisting of poly-L-amino acids, such as poly-L-lysine, poly-L-arginine, poly-L-glutamic acid, poly-L-histidine, poly--D-glutamic acid or a mixture thereof. This polyamino acid polymer is added in concentration from about 0.001% to about 30%, preferably from about 0.1% to about 1% volume per volume of concentrated plasma.

In still another alternative, the polymer may be chitosan or chitin, such as chitosan-polyamine or preferably chitosan-cationic, which forms strong and clear films and gels when brought in contact with divalent cations. These polymers are biodegradable and non-toxic. Chitosan is added in concentration from about 0.1% to about 10%. Addition of chitosan accelerates wound healing and having by itself certain bioadhesive properties, increases adhesivity of the platelet rich plasma-chitosan hemostatic adhesive.

The polymer is dissolved in small volume, about 0.5–1 ml, of concentrated plasma and then added to the platelet-rich plasma.

3. Preparation of Hemostatic Adhesive Agent

The hemostatic adhesive agent of the invention is prepared by mixing together the concentrated plasma, isolated platelets and the polymer.

Typically, platelets isolated from the volume of the plasma prior to its concentration are added to the mixture of the 5–10 times concentrated plasma and then the polymer is added, forming platelet-rich plasma concentrate containing the polymer. The platelets to plasma ratio is from 1:2 to 2:1 preferably about 1:1, depending on the plasma concentration. Platelet-rich plasma to polymer ratio is from 99:1 to 80:20.

Concentrated plasma contains all plasma proteins, in a concentration levels at which they are normally present in the plasma. These proteins are fibrinogen (factor I), prothrombin (factor II), and other plasma coagulation factors as described above.

The mixture of the platelet-rich plasma and polymer forms the hemostatic adhesive agent of the invention. The agent may additionally contain other therapeutically active pharmaceutically acceptable agents or pharmaceutically acceptable additives such as antibiotics or enzymes.

The agent of the invention is able to stop extensive and large area bleeding from the surface wound or from the surface of a deep tissue wound without addition of exogenous thrombin or any other agent.

In practice, the wound is typically sprayed with a solution of ionized calcium, or other divalent cations able to gel the polymer, typically with 1%–20%, preferably 10% $CaCl_2$ solution, and the hemostatic agent is applied over the wound, incision, cut, bleeding surface or other injury. In these cases, the presence of the polymer which gels and activates and aggregates the exogenous platelets over the site of injury forms the initial clot and enhances the coagulation activity of platelets and their normal hemostatic properties. The presence of exogenous platelets and high concentrations of available plasma proteins needed for coagulation allows hemostatic action and clotting build-up on and over the hemostatic polymer clot.

In cases of profuse bleeding, such as in the cases of arterial or venous cuts or ruptures, the hemostatic agent of the invention is also useful. To enhance its hemostatic action, in some case, it is preferred to add to the calcium solution an exogenous and preferably autologous thrombin, in amount from about 0.2 to about 2 g, preferably about 1.8 g, of thrombin per 100 ml of 10% $CaCl_2$. Such addition further enhances the coagulation.

While it is preferred that the autologous platelet-rich plasma is used whenever possible, the non-autologous platelet-rich plasma from other humans is equally useful and is prepared by the same process and under the same conditions.

The hemostatic adhesive agents containing platelet-rich plasma and polymers provide rapid hemostasis due to the presence of the polymer which, as one of its own properties, gels in the presence of calcium or other divalent cations and as a foreign substance, causes platelet aggregation and clotting. The clot formation with gradually increasing tensil strength of the adhesive is fast, as the polymer component of the agent gels rapidly in the presence of the calcium ions and thus provides the initial clot and continues until complete hemostasis is achieved.

The addition of the polymer to the current adhesive increases its adhesivity and strength provided by the polymer addition. The time for which the hemostatic adhesive is applied controls the extent of the hemostasis and the strength of the adhesion. As a result, the hemostatic agent of the invention is useful for sealing and adhesion of deep tissue wounds, ruptures, or incisions, tears or cuts on the veins. The process for preparation of the hemostatic adhesive agent is fast, typically the hemostatic polymer adhesive can be produced within 10–15 minutes and does not require any special equipment, agents or procedures than those used in the biochemical medical laboratory on a daily basis.

In cases of autologous platelet-rich plasma, additional advantages are the reduced risk of disease transmission as both platelets and the plasma are obtained from the patient. The immunogenic reactions to the exogenous sources of the thrombin or fibrinogen, typically bovine thrombin or fibrinogen, are eliminated. Presence of the living, autologous platelets additionally promote and expedite healing of tissues.

When the adhesive agent is prepared in advance, essentially the same procedure is followed except that the plasma concentrate and platelets are stored separately in the refrigerator, if the adhesive will be used within 24 hours, or frozen, if the adhesive will be used later. The polymer is stored and preweighed in desired amount, preferably in amount which would provide 2%–20% dilution with plasma concentrate. The volume of the adhesive depends on the extent of the surgery. Typically, platelet-rich plasma concentrate is obtained from 30 ml blood, which provides about 1.5–2.5 ml of the concentrate. If the wound is over the large area which needs to be sealed, appropriately larger volumes of concentrate are prepared.

It is another advantage of the invention that the treating surgeon or physician can determine what volume is necessary to achieve the complete adhesion and hemostasis. Also, should the bleeding not be contained by the available volume of the agent, the additional volume can be quickly and conveniently prepared.

UTILITY

The hemostatic adhesive agent of the invention is used for treatment of any trauma of liver, spleen, pancreas, lung, bone, etc., for cardiovascular and vascular, such as microvascular anastomoses, vascular grafts, intraoperative bleeding, and aortic repair, for thoracic surgery such as lung biopsy, for transplant of heart, renal, pancreas, lung, bone or bone marrow, for neurosurgery such as nerve anastomosis, or CSF leak repair, for endoscopic surgery, such as hemostasis in hepatic trauma, or bile duct repair, for interventional radiology, such as hemostasis for percutaneous liver biopsy or vascular occlusion, for gastrointestinal surgery such as colonic anastomoses, for obstetrics and gynecology such as rectovaginal fistulas, for pediatric and fetal surgery, for plastic surgery and burn repairs such as grafting process of cultured epidermis, for dermatology such as hair transplants, for dental surgery, for ophthalmic cataract surgery, for urology, for correction of urinary fistulas and such others.

The treatment may be used alone or in combination with other techniques and drugs typically used to correct these problems.

A major difference between hemostatic adhesive agent preparations and previous fibrin glues is the inclusion of living, metabolizing platelets, high concentration of plasma proteins and the presence of the polymer. The importance of platelets in thrombosis is increasingly recognized. For example, platelets contain a vast number of biologically active molecules within cytoplasmic granules. The currently known list of alphagranular proteins continues to enlarge and includes many adhesive proteins such as fibrinogen, von Willebrand factor and thrombospodin, plasma proteins, cellular mitogens, such as platelet derived growth factor and TGF β-coagulation factors and protease inhibitors. More recently the inner living of the alpha-granule unite membrane has been demonstrated to contain a number of physiologically important receptors including glycoprotein IIb/IIIa($\alpha_{IIb}\beta_3$) and P-selectin. The alpha-granular contents release during platelet activation at the sites of vessel wall injury and thus play an important role in hemostasis, inflammation, and ultimate wound repair. The possible therapeutic effect arising from the fact the exogenous platelets and particularly autologous platelets are present in the hemostatic adhesive agent is therefore an additional advantage of the invention.

The following examples are intended to illustrate the invention and its utility. These examples are not to be interpreted as limiting the invention in any way.

EXAMPLE 1

Preparation of Autologous Plasma and

Polymer Containing Surgical Adhesive

This example illustrates preparation of hemostatic platelet-rich plasma/alginate containing surgical agent.

A 30 ml blood sample was drawn and placed into 0.1055 M buffered sodium citrate solution. The tubes were centrifuged at 770× g for 10 minutes and a 15 ml platelet-rich plasma sample was removed. The plasma was centrifuged a second time at 2000× g. Then, the plasma was removed and the platelets were saved. The plasma was concentrated by centrifugation through a 30,000 MW cut off filter obtained from CentriCell Polysciences, Inc. for 20 minutes. The plasma was concentrated by a factor of 7–8, that is 270–390 mg of fibrinogen present in 100 ml of plasma was concentrated to levels larger than 2000 mg of fibrinogen per 100 ml of plasma. Sodium alginate (1%) obtained from Kelco Gel LV, Merck & Co., Inc., San Diego, Calif., was dissolved in 4 ml of the concentrated plasma. The platelets obtained from the used equal volume of blood, that is from 30 ml of full blood, were added back to the 4 ml of concentrated plasma and alginate. The mixture was stirred and used for determination of its hemostatic properties.

To obtain the autologous hemostatic surgical adhesive, blood was obtained from the individual to be treated with the autologous surgical agent.

EXAMPLE 2

Hemostatic Properties of the Plasma and Polymer Containing Hemostatic Agent on the Tissue Injury This example illustrates the adhesive effect of the platelet-rich plasma and alginate containing hemostatic adhesives on the experimentally induced liver trauma and incisions in rats.

The hemostatic agent was prepared as described in Example 1 from the rat blood.

A 250 g rats were anesthetized. A midline incision was made and the surface of the liver was exposed. One lobe of the liver was excised and removed and 1 cm cut was made in another lobe of the liver. The bleeding surface of the wounds were sponged dry and sprayed with a 10% $CaCl_2$ solution and the hemostatic agent containing concentrated plasma, platelets and alginate was applied by spray. The plasma/platelet/alginate adhesive gelled on a contact with the liver and complete hemostasis was attained within 2 minutes.

EXAMPLE 3

Hemostatic Properties of the Plasma and Polymer Containing Hemostatic Adhesive on Arterial Incision This example illustrates the adhesive effect of the platelet rich plasma and alginate containing hemostatic adhesive on arterial incision.

The platelet-rich plasma was obtained from 30 ml of rat blood as described in Example 1. Sodium alginate (0.1–1% Kelco Gel LV) was dissolved in the concentrated plasma. Platelets isolated from an equal volume of blood, as was the volume of the blood used to prepare the concentrated plasma were added back to the plasma and alginate mixture.

A 250 g rat was anesthetized. An incision was made over the femoral artery. The femoral artery was exposed and cleared. The blood flow through the artery was stopped by pressure on the proximal portion of the artery. The artery was cut and divided cleanly horizontally with a scalpel blade and the excess blood sponged dry. The divided artery was sprayed with 10% $CaCl_2$/thrombin solution (0.009 g thrombin in 0.5 ml 10% $CaCl_2$) and the platelet-rich plasma concentrate alginate containing hemostatic agent was applied. The pressure on the proximal artery was maintained for 2–5 minutes. The solution of hemostatic adhesive gelled on contact with the calcium solution on the surface of the artery and bleeding stopped. After the compression of the blood flow was relieved, hemostasis was completely maintained with 4–5 minutes. The incision did not reopen.

EXAMPLE 4

Hemostatic Properties of the Platelet-rich Plasma and Poly-L-Lysine Hemostatic Adhesive on the Tissue Injury This example illustrates the adhesive effect of the platelet rich plasma and poly-L-lysine containing surgical hemostatic adhesive on liver trauma.

A 30 ml blood sample was drawn and placed into 0.1055 M buffered sodium citrate solution. The tubes were centrifuged at 770× g and a 15 ml plasma sample was removed. The plasma was centrifuged a second time at 2000× g. Then, the plasma was removed and the platelets were saved. The plasma was concentrated by centrifugation through a 30,000 MW cut off filter obtained from CentriCell Polysciences, Inc. for 20 minutes. The plasma was concentrated by a factor of 7–8 as described above. Poly-L-lysine hydrobromide (0.03 g) MW464,000 was dissolved in 0.5 ml plasma. All platelets removed from the plasma before its concentration were added back to the concentrated plasma and poly-L-lysine/plasma was added. The mixture was stirred and used for determination of its hemostatic properties.

A 250 g rat was anesthetized. A midline was made and the surface of the liver was exposed. A lobe of the liver was excised and 1 cm cut was made in another lobe of the liver. The bleeding surface of the wounds were sponged dry and sprayed with a 10% $CaCl_2$ as the platelet-rich plasma and poly-L-lysine containing hemostatic adhesive was applied. The platelet-rich plasma concentrate poly-L-lysine containing hemostatic solution gelled on a contact with the liver on the surface of both wounds and hemostasis was attained on the surface of the liver within 1–2 minutes and 3–5 minutes at the site of excised lobe.

EXAMPLE 5

Hemostatic Properties of the Platelet-rich Plasma and Poly-L-Lysine Hemostatic Adhesive This example illustrates the adhesive effect of the platelet rich plasma and poly-L-lysine containing surgical hemostatic adhesive on arterial incision.

A 30 ml blood sample was drawn and placed into 0.1055 M buffered sodium citrate solution. The tubes were centrifuged at 770× g and a 15 ml plasma sample was removed. The plasma was centrifuged a second time at 2000× g. Then, the plasma was removed and the platelets were saved. The plasma was concentrated by centrifugation through a 30,000 MW cut off filter obtained from CentriCell Polysciences, Inc. for 20 minutes. The plasma was concentrated by a factor of 7–8 as described above. Poly- L-lysine hydrobromide MW464,000 (0.05 g) was dissolved in 0.5 ml plasma. All platelets removed from the plasma before its concentration were added back to the concentrated plasma and poly-L-lysine was added. The mixture was stirred and used for determination of its hemostatic properties.

A skin incision was made over the femoral artery. The femoral artery was exposed and cleared. The blood flow through the artery was stopped by pressure on the proximal portion of the artery. The artery was cut (~1 cm) and divided cleanly horizontally with a scalpel blade and the excess blood sponged dry. The divided artery was sprayed with 10% $CaCL_2$/thrombin (1.8 g thrombin/100 ml 10% $CaCl_2$) and the hemostatic agent containing platelet-rich plasma and poly-L-lysine was applied to the incision. The pressure on the proximal artery was maintained for 2 minutes with occasional checking whether the wound still bleeds, the bleeding stopped completely at about 4–5 minutes. After the compression of the blood flow was relieved, the bleeding did not recur and hemostasis was maintained.

EXAMPLE 6

Hemostatic Properties of the Plasma/Polymer Surgical Adhesive on Arterial Incision This example illustrates the adhesive effect of the platelet rich plasma combined with calcium/thrombin poly-L-lysine solution at the site of arterial incision. The solutions were as in Example 5.

A 300 g rat was anesthetized and an incision was made over the femoral artery. The femoral artery was exposed and cleared. The blood flow through the artery was stopped by pressure on the proximal portion of the artery. The artery was cut and divided cleanly with a scalpel blade and the excess blood sponged dry. The divided artery was sprayed with $CaCl_2$ poly-L-lysine solution and the platelet-rich plasma was applied. The platelet rich plasma reacted quickly with poly-L-lysine/calcium chloride solution, poly-L-lysine gelled upon contact with the divided artery and stopped bleeding. The pressure on the proximal artery was maintained for 1 minute. Thereafter in 30 second intervals, the state of the adhesion was checked until complete hemostasis occurred in about 10 minutes. After the compression of the blood flow was relieved, there was no bleeding and hemostasis was maintained.

EXAMPLE 7

Hemostatic Properties of the Plasma/Polymer Surgical Agent on Arterial Incision

This example illustrates hemostatic effect of poly-L-lysine administered separately in the calcium solution.

The solutions were as in Example 5.

An incision was made over the rat (300 g) femoral artery. The femoral artery was exposed and cleared. The blood flow through the artery was stopped by pressure on the proximal protion of the artery. The artery was cut and divided cleanly with a scalpel blade and the excess blood sponged dry. The divided artery was sprayed with $CaCl_2$ thrombin/poly-L-lysine solution and the platelet-rich plasma was applied. The platelet rich plasma reacted quickly with poly-L-lysine/calcium chloride/thrombin solution, polylysine gelled up on contact with the divided artery and stopped bleeding. The pressure on the proximal artery was maintained for 1 minute. Thereafter in 30 second intervals, the state of the adhesion was checked until complete hemostasis occurred in about 4.5 minutes. After the compression of the blood flow was relieved, there was no bleeding and hemostasis was maintained.

EXAMPLE 8

Hemostatic Properties of the Plasma and Polymer Containing Surgical Adhesive on Tissue Injury Incision This example illustrates the adhesive effect of the platelet rich plasma acting as a hemostatic adhesive on tissue injury in situ in the presence of dry poly-L-lysine.

Platelet-rich plasma was prepared from the rat blood as described in Example 1.

A 250 g rat was anesthetized. A midline incision was made and the surface of the liver was exposed. A lobe of the liver was excised and about one cm long cut was made in another lobe of the liver. The bleeding surface of the wounds were sponged dry and 0.1 g of dry poly-L-lysine powder was placed over the wound. The wound was sprayed with a $CaCl_2$/thrombin solution (0.009 g thrombin in 0.5 ml 10% $CaCl_2$) and the platelet-rich plasma concentrate was applied at the same time. The hemostasis occurred with the combination of dry poly-L-lysine with calcium thrombin solution in the presence of platelet-rich plasma concentrate very quickly. The total hemostasis occurred and the bleeding completely stopped within 4 minutes.

EXAMPLE 9

Hemostatic Properties of the Plasma/Polymer Surgical Adhesive on Arterial Incision This example illustrates the adhesive effect of the platelet-rich plasma acting as a hemostatic adhesive in the presence of the dry poly-L-lysine.

An incision was made over the rat femoral artery. The femoral artery was exposed and cleared. The blood flow through the artery was stopped by pressure on the proximal protion of the artery. The artery was vertically (~1.5 cm) cut and divided cleanly with a scalpel blade. The excess blood was sponged dry. The divided artery was covered with approximately 0.5 g dry poly-L-lysine and sprayed with 10% $CaCl_2$/thrombin solution (as in example 8) at the same time as the platelet-rich plasma concentrate was applied. After about 5.5 minutes, when the compression of the blood flow was relieved, bleeding stopped and hemostasis was maintained thereafter.

EXAMPLE 10

Laparoscopically Applied Plasma/Polymer Adhesive in Liver Trauma

This example illustrates the use of platelet-rich plasma and polymer containing hemostatic adhesive on liver trauma in mammals.

Domestic swine are anesthetized using intravenous (IV) thiamylal sodium (16.0 mg/kg) and inhaled halothane. Laparoscope is introduced into the peritoneal cavity under sterile conditions. Heparin is administered to create maximal bleeding from the liver laceration. Laceration in the liver lobe about 3 cm long and 2 cm deep is made to induce bleeding from this injury.

About 5 ml of platelet-rich plasma alginate containing hemostatic agent is administered through the laparoscope to the site of the liver laceration. Bleeding ceases very quickly in every case.

EXAMPLE 11

Hemostatic Effect of the Adhesive Agent on Liver Injury in Humans

This example illustrates the adhesive effect of autologous hemostatic agent prepared from the platelet-rich plasma obtained from patient's own blood in combination with an alginate.

Patient suffers from ruptured liver. Blood is drawn and autologous platelet-rich plasma concentrate is prepared as described in Example 1. Platelet-rich plasma concentrate is mixed with 1% of sodium alginate. Upon laparoscopy, the bleeding liver wound is sprayed with calcium/thrombin solution (1.8 g thrombin dissolved in 100 ml of 10% $CaCl_2$) and the adhesive platelet-rich plasma alginate is applied over the bleeding rupture to stop bleeding. Bleeding is stopped within several minutes.

EXAMPLE 12

Hemostatic Effect of Combination of Platelet-rich Plasma with Poly-L-lysine in Calcium/Thrombin In Situ This example illustrates the hemostatic effect of hemostatic effect of combination of platelet-rich plasma with poly-L-lysine in calcium/thrombin in situ in human following the bleeding from ruptured spleen.

Patient suffers from ruptured spleen. Venous blood is drawn and the autologous platelet-rich plasma is prepared according to Example 1. 0.03 g of poly-L-lysine is dissolved in the 10% calcium chloride. Peritoneal cavity is opened, the poly-L-lysine calcium solution is applied on the bleeding surface of the spleen by spraying and the platelet-rich plasma is added to it in situ to stop bleeding. Bleeding slows down and stops in about 25–30 minutes.

EXAMPLE 13

Hemostatic Effect of In Situ Combination of Platelet-rich Plasma, Poly-L-lysine and Calcium Thrombin This example illustrates the hemostatic effect of the in situ combination of dry poly-L-lysine with platelet-rich plasma in the presence of calcium/thrombin.

Patient has deep liver wound and bleeds profusely. Blood is used for preparation of platelet-rich plasma concentrate as in Example 1. The wound is covered with dry poly-L-lysine and sprayed with calcium/thrombin solution (1.8 g/100 ml 10% $CaCl_2$) and the platelet-rich plasma concentrate is applied. Within 3–5 minutes, bleeding is stopped.

EXAMPLE 14

Platelet-rich Plasma and Alginate Containing Agent for Sealing of the Common Bile Duct This example illustrates a sealing activity of the platelet-rich plasma and poly-l-lysine containing adhesive of the invention during and post biliary tract surgery in higher mammals.

Dogs are subjected to the common bile duct surgery. Platelet-rich plasma is prepared from their blood according to Example 1 and mixed with 0.03 g poly-L-lysine, as described. Poly-L-lysine containing platelet-rich plasma is applied to the place of the incision to stop bleeding and leaking of the bile. Sealing is achieved within 8 minutes.

EXAMPLE 15

Use of Autoloqous Platelet-rich Plasma Polymer Adhesive to Control Pulmonary Leak This example illustrates the use of the platelet-rich plasma alginate containing adhesive as the measure for control of lung air leaks.

Patient has an obstructive disease due to a lung tumor. After the tumor is removed, the patient has an air leak. A site of the air leak is identified by using bronchoscope. Patient's blood is used to prepare platelet-rich plasma concentrate and the alginate containing adhesive. Catheter is placed as close as possible to the site of the leak and the calcium/thrombin solution (1 ml) is injected through the catheter, followed quickly by 2 ml of platelet-rich plasma combined with alginate.

Air leak is blocked and sealed by the adhesive within 5–10 minutes.

EXAMPLE 16

Hemostatic Properties of the Platelet-rich Plasma Chitosan Adhesive

This example illustrates hemostatic properties of the platelet-rich plasma chitosan adhesive.

A 30 ml blood sample was drawn in 0.1055 M buffered sodium citrate solution. The tubes were centrifuges at 700× g and a 15 ml platelet-rich plasma sample was removed. The plasma was centrifuged a second time at 2000× g, the plasma was removed and the platelets were saved. The plasma was concentrated by centrifugation through a 30,000 MW cut off filter (CentriCell- Polysciences, Inc.) for 20 minutes. The plasma is concentrated by a factor of 7–8 times (270–390 mg/100 ml normal is concentrated to >2000 mg/100 ml). Chitosan (Sigma Chemical Company, P.O. Box 08, St. Louis, Mo.) was used at a concentration of 2 mg/ml in 0.2% glacial acetic acid. The chitosan (0.5 ml) was dissolved in 0.5 ml plasma. Platelets from an equal volume of blood, as the concentrated plasma, was added back to the plasma/chitosan.

A 250 g rat was anesthetized and two incisions were made. A midline was made and the surface of the liver was exposed. A lobe of the liver was excised and an 1 cm cut was made in another lobe of the liver. The bleeding surface of the wounds were sponged dry and sprayed with an $CaCl_2$/thrombin solution (0.009 g thrombin in 0.5 ml 10% $CaCl_2$) as the plasma/platelet/chitosan was applied. The plasma/platelet/chitosan solution gelled a contact with the liver and hemostasis was attained.

EXAMPLE 17

Hemostatic Properties of the Platelet-rich Plasma Chitosan Adhesive

This example illustrates hemostatic properties of the platelet-rich plasma chitosan adhesive.

A second incision was made over the rat femoral artery. The femoral artery was exposed and cleared. The blood flow through the artery was stopped by pressure on the proximal portion of the artery. The artery was divided cleanly with an scalpel blade and the excess blood sponged dry. The divided artery was sprayed with 10% $CaCl_2$/thrombin as the plasma/platelet/chitosan was applied. The pressure on the proximal artery was maintained for about 5 minutes. After the compression of the blood flow was relieved, hemostasis was maintained.

EXAMPLE 18

Hemostatic Properties of the Platelet-rich Plasma Chitosan Adhesive

This example illustrates hemostatic properties of the platelet-rich plasma chitosan adhesive.

A 30 ml blood sample was drawn in 0.1055 M buffered sodium citrate solution. The tubes were centrifuged at 770× g and a 15 ml platelet rich plasma sample was removed. The plasma was centrifuged a second time at 2000× g, the plasma was removed and the platelets were saved. The plasma was concentrated by centrifugation through a 30,000 MW cut off filter (CentriCell-Polysciences, Inc.) for 20 minutes. The plasma is concentrated by a factor of 7–8 times (270–390 mg/100 ml normal is concentrated to >2000 mg/100 ml). Platelets from an equal volume of blood, as the concentrated plasma, was added back to the plasma. Chitosan (Sigma Chemical Company, P.O. Box 14508, St. Louis, Mo.) was used at a concentrated of 2 mg/ml in 0.25% glacial acetic acid. The chitosan (0.5 ml) was dissolved in .5 ml of $CaCl_2$/thrombin solution (0.009 g thrombin in 0.5 ml 10% $CaCl_2$).

A 250 g rat was anesthetized and two incisions were made. A midline was made and the surface of the liver was exposed. A lobe of the liver was excised and a 1 cm cut was made in another lobe of the liver. The bleeding surface of the wounds were sponged dry and sprayed with a $CaCl_2$/thrombin/chitosan solution thrombin as the plasma/platelet concentrate was applied. The plasma/platelet/chitosan solution gelled an contact with the liver and hemostasis was attained within 6 minutes.

EXAMPLE 19

Hemostatic Properties of the Platelet-rich Plasma Chitosan Adhesive

This example illustrates hemostatic properties of the platelet-rich plasma chitosan adhesive.

A second incision was made over the rat femoral artery. The femoral artery was exposed and cleared. The blood flow through the artery was stopped by pressure on the proximal portion of the artery. The artery was divided cleanly with a scalpel blade and the excess blood sponged dry. The divided artery was sprayed with the $CaCl_2$/thrombin/chitosan solution as the plasma/platelet concentrate was applied. The plasma/platelet/chitosan solution gelled in contact with the divided artery and hemostasis was attained. The pressure on the proximal artery was maintained for about 6 minutes and the bleeding was checked periodically. After the compression of the blood flow was relieved, hemostasis was maintained.

EXAMPLE 20

Hemostatic Properties of the Platelet-rich Plasma Chitosan Adhesive

This example illustrates hemostatic properties of the platelet-rich plasma chitosan adhesive.

A 30 ml blood sample was drawn in 0.1055 M buffered sodium citrate solution. The tubes were centrifuged at 770× g and a 15 ml platelet-rich plasma sample was removed. The plasma was centrifuged a second time at 2000× g, the plasma was removed and the platelets were saved. The plasma was concentrated by centrifugation through a 30,000 MW cut off filter (CentriCell- Polysciences, Inc.) for 20 minutes. The plasma is concentrated by a factor of 7–8 times (270–390 mg/100 ml normal is concentrated to >2000 mg/100 ml). Platelets from an equal volume of blood, as the starting plasma, was added back to the plasma concentrated.

A 250 g rat was anesthetized and two incisions were made. A midline was made and the surface of the liver was exposed. A lobe of the liver was excised and a 1 cm cut was made in another lobe of the liver. The bleeding surface of the wounds were sponged dry and dry chitosan powder 0.03 g was placed over the wound. The wound was sprayed with a $CaCl_2$/thrombin solution (0.009 g thrombin in 0.5 ml 10% $CaCl_2$) as the plasma/platelet concentrate was applied. The plasma/platelet solution gelled was applied. The plasma/ platelet solution gelled on contact with the liver and hemostasis was attained.

EXAMPLE 21

Hemostatic properties of the Platelet-rich Plasma Chitsan Adhesive

This example illustrates hemostatic properties of the platelet-rich plasma chitosan adhesive.

A second incision was made over the femoral artery. The femoral artery was exposed and cleared. The blood flow through the artery was stopped by pressure on the proximal portion of the artery. The artery was divided cleanly with a scalpel and the excess blood sponged dry. The divided artery covered with 30 µg dry Chitosan powder. The artery was then sprayed with 10% $CaCl_2$/thrombin as the plasma/platelet concentrate was applied. The pressure on the proximal artery was maintained for 2–5 minutes. After the compression of the blood flow was relieved, hemostasis was maintained.

What is claimed is:

1. A hemostatic adhesive agent for triggering clotting process comprising of a platelet-rich plasma concentrate and a physiologically acceptable biocompatible polymer selected from the group-consisting of alginates, poly-L-amino acids, chitosan and chitin wherein the platelet-rich plasma concentrate is 5 to 10 times concentrated normal plasma, said concentrate containing 5 to 10 times higher concentration of fibrinogen and other plasma proteins than the normal plasma;

wherein a platelets to plasma concentrate ratio is from 1:2 to 2:1; and wherein a platelet-rich plasma concentrate to polymer ratio is from 99:1 to 80:20; wt/wt.

2. The agent of claim 1 wherein the plasma is concentrated about 10 times.

3. The agent of claim 2 wherein the plasma is concentrated from about 7 to about 8 times.

4. The agent of claim 3 wherein the platelet-rich plasma is autologous.

5. The agent of claim 1 wherein the polymer is selected from the group consisting of sodium alginate, calcium alginate, strontium alginate, barium alginate, magnesium alginate, and a mixture thereof.

6. The agent of claim 5 wherein the polymer is sodium alginate added in concentration from about 0.001% to about 20%.

7. The agent of claim 6 wherein sodium alginate is added in amount from about 0.1% to about 10%.

8. The agent of claim 4 wherein the polymer is selected from the group consisting of poly-L-lysine, poly-L-histidine, poly-α-D-glutamic acid and a mixture thereof.

9. The agent of claim 8 wherein the polymer is poly-L-lysine added in concentration from about 0.001% to about 30%.

10. The agent of claim 9 wherein poly-L-lysine is added in amount from about 0.1% to about 1%.

11. The agent of claim 4 wherein the polymer is chitosan.

12. The agent of claim 11 wherein chitosan is added in amount from about 0.1% to about 10%.

13. A method for attaining hemostasis by triggering clotting process, said method comprising administering, in the presence of a divalent ion, to a site of injury a platelet-rich plasma and a physiologically acceptable biocompatible polymer selected from the group consisting of alginates, poly-L-amino acids, chitosan and chitin, wherein the platelet-rich plasma concentrate is 5 to 10 times concentrated normal plasma, said concentrate containing 5 to 10 times higher concentration of fibrinogen and other plasma proteins than the normal plasma;

wherein a platelets to plasma concentrate ratio is from 1:2 to 2:1; and wherein a platelet-rich plasma concentrate to polymer ratio is from 99:1 to 80:20 wt/wt.

14. The method of claim 13 Wherein the platelet-rich plasma is autologous.

15. The method of claim 13 wherein the polymer is the alginate selected from the group consisting of sodium alginate, calcium alginate, strontium alginate, barium alginate, magnesium alginate, and a mixture thereof added in concentration from about 0.001% to about 20%.

16. The method of claim 13 wherein the polymer is the poly-L-amino acid selected from the group consisting of poly-L-lysine, poly-L-histidine, poly-α-D-glutamic acid and a mixture thereof added in concentration from about 0.001% to about 30%.

17. The method of claim 14 wherein the divalent ion is calcium.

* * * * *